United States Patent [19]

Sitte

[11] 4,363,783
[45] Dec. 14, 1982

[54] APPARATUS FOR SPECIMEN TREATMENT

[75] Inventor: Hellmuth Sitte, Seefeld, Austria

[73] Assignee: C. Reichert Optische Werke, AG, Vienna, Austria

[21] Appl. No.: 316,604

[22] Filed: Oct. 30, 1981

[30] Foreign Application Priority Data

Nov. 12, 1980 [DE] Fed. Rep. of Germany ....... 3042578

[51] Int. Cl.³ .............................................. F04C 2/00
[52] U.S. Cl. ...................................... 422/68; 435/287
[58] Field of Search ........................... 422/68; 435/287

[56] References Cited

U.S. PATENT DOCUMENTS

| 1,515,914 | 11/1924 | Ungar | 422/68 |
| 2,995,425 | 8/1961 | Fuhrmann | 422/68 |
| 4,071,324 | 1/1978 | Reid | 422/68 |

FOREIGN PATENT DOCUMENTS

| 476225 | 8/1951 | Canada | 422/68 |
| 2455583 | 10/1975 | Fed. Rep. of Germany | 422/68 |

*Primary Examiner*—Robert L. Lindsay, Jr.
*Attorney, Agent, or Firm*—Alan H. Spencer

[57] ABSTRACT

Apparatus for fixation, dessication, and embedding of biologic specimens for microscopic, especially electron microscopic studies having compartment for treating specimens held in liquid permeable specimen holders, a supply of treatment liquid connected to the compartment, to introduce liquid from the supply, and remove liquid from the compartment, a chamber (14c) in the compartment for holding a quantity of fluid, a passage connected to the chamber, pump (15) located in the chamber for moving fluid through the passage, at least one tubular cell (14a) for supporting a plurality of specimen holders (10, 10a) is an end to end relationship, one end of said cell being connected to said passage, the other end of each of said chamber and said cell being connected to a common portion of said tank to permit liquid to be circulated by said pump.

10 Claims, 10 Drawing Figures

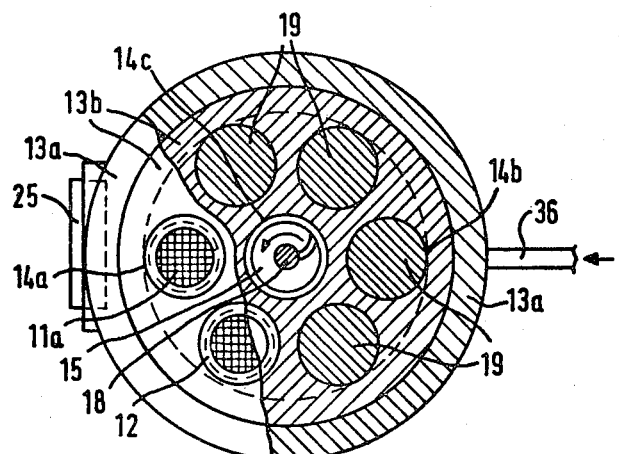
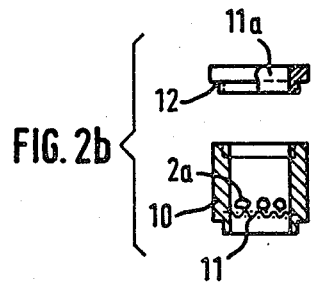
FIG. 2a
FIG. 2b
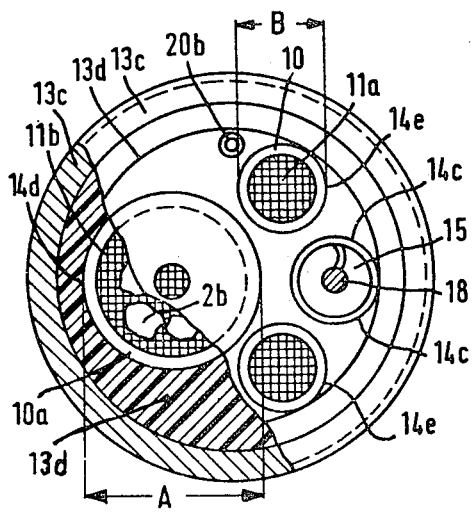
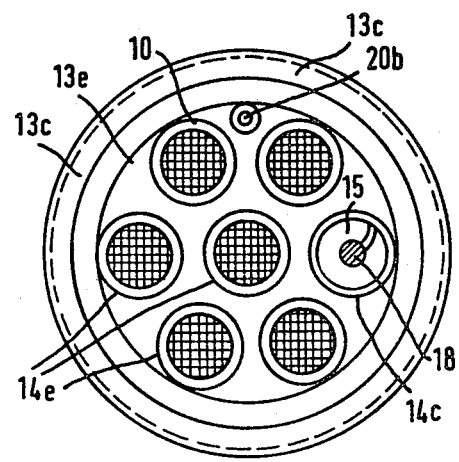
FIG. 3a
FIG. 3b

APPARATUS FOR SPECIMEN TREATMENT

BACKGROUND OF THE INVENTION

1. Field of the Invention

This invention concerns apparatus for fixation, dessication, and embedding of biologic specimens.

2. Description of the Prior Art

In most cases biologic specimens cannot be examined directly in a microscope, especially an electron microscope, but require prior treatment.

Generally such pretreatment consists primarily in stabilization of vital structures by suitable chemicals (fixation, for example, by aldehyde and/or heavy metal compounds in aqueous solution) or by rapid freezing (cryofixation) in subsequent dessication in organic solvents (for example acetone or aldehyde, under certain circumstances with the addition of heavy metal compounds to increase contrast in the electron microscopic image or to stabilize the structures after cryofixation) and finally, in impregnation with materials (embedding, for example, in wax or plastic) which support the specimen while it is being cut into a thin or ultra thin section by a microtome or ultra microtome. This process generally requires, on the one hand, repeated changing of different liquid media. On the other hand, it must be carefully observed that the specimen surfaces are always in contact with fresh liquid since otherwise the desired exchange of cellular or tissue liquids within the specimens vis-a-vis the different treatment liquids proceeds too slowly. In many cases, incubation is carried out, in addition, at reduced temperature (reduction of autolytic reactions during fixation or reduction of the production of specimen inherent structures during dehydration) or at increased temperature (reduction of viscosity of embedding media or melting of the wax used for embedding).

This preparation process can accordingly, be carried out by hand, however, it requires continuous monitoring and an altogether very high expenditure of work by manual filling, refilling, shaking, or additionally, by placement of the tank in the cooling or heating devices. With regard to optimum reproducibility of results and in view of continuously rising labor costs, automatic apparatus ("tissue processors") have been developed which carry out the entire treatment process automatically and reproducibly. Such automatic apparatus can be obtained commercially in numerous different designs for purposes of light and electron microscopy and is used primarily in larger laboratories or for repetitious work. One existing apparatus includes a treatment compartment in which holders for the biologic specimens to be treated can be stacked one on top of the other in columnar form. The holders are liquid permeable by means of porous inserts on the bottom and top and the apparatus includes a device to generate periodic raising and lowering of the liquid level in the treatment chamber so that the specimens in the tanks are flushed. Due to high costs as well as, to some extent, relatively high consumption of fixation, dessication, and embedding materials, such automatic devices have, however, only been used in limited areas. In all other sectors, the manual approach is still most common, aside from rotary discs to generate continuous weak convection of the treatment media. The manual labor which consists at least in changing of the different media treatment liquids which are necessary in small time increments of 10 to 20 minutes each, frequently with additional shaking, and last but not least, cleaning of the different vessels is not desirable due to the fact that the liquids most frequently used, fixation solutions, intermediate, and dessication liquids, as well as some embedding materials are hazardous to health and either come into contact with the skin (allergic reactions) or may be inhaled (general injury). This aspect necessitates additional precautionary measures which further complicate work.

The objective of this invention is thus, to design a treatment apparatus which is relatively simple and thus considerably below the costs of the aforementioned automatic apparatus in terms of purchase price, consumption of fixation, dessication, and embedding liquids which do not exceed amounts used in purely manual liquid replacement, which however, precludes or minimizes skin contact with the liquids used as well as the risk of inhalation of toxic vapors. Thus, this treatment apparatus is designed to simplify the aforementioned preparation steps to a degree comparable to that of automatic equipment and, moreover, be at least functionally on par, i.e., relative to preparation effect. However, in spite of simple structure, the treatment apparatus should be receptive to additional control equipment for providing convenience and automation.

SUMMARY OF THE INVENTION

According to the invention, the problem is solved by treatment apparatus, the features of which are listed in the characteristic section of patent claim 1.

The proposed apparatus satisfies the established requirements primarily because the specimen holders with permeable base and top accomodate individual specimens and are stacked one on top of the other in one or more receiver tubes or cells, in which case a pump of a recognized type (screw, propeller, membrane, piston, and the like) generates a liquid flow in another compartment linked to the receiver tubes, for example, likewise a cell, which in turn continuously flushes the specimens.

According to a beneficial improvement of the invention, different receiver tubes can have different diameters so that receiver tanks of varied diameter and thus variable volume within wide limits can be used. In this case the unusued receiver tube can be filled, for example, by a dummy body, which reduces the empty volume to zero. In a similar manner, the space in the receiver tubes which is not occupied by the specimen holders can be filled by dummies which have a hole to permit the desired liquid circulation.

One benefit of the invention is the fact that the mechanical elements to generate liquid motion are actuated and controlled in such a manner that both the direction of motion can be reversed and the rate of liquid flow altered. In this case we have found that periodic reversal of the direction of the motion yields the best results. Moreover, in advanced development of the invention, heating or cooling devices, as well as temperature sensitive elements allow operation at different temperatures, which under certain circumstances can be preselected and thermostatically maintained constant, facilitate fill level indication, under certain circumstances as an overfill safety device in operational conjunction with a filling valve, checking of the liquid level, and addition of proportioned amounts of liquid, a hose connection at the discharge valve can allow liquid change without operator contact with the used liquids which are drained directly into a waste tank (sump). Finally, utilization of appropriate coatings on the important functional elements or corresponding operational components and seals can make long term use of corrosive media as well as simple cleaning of the system possible.

The most complete protection against toxic skin contact or vapors can ultimately be achieved in a beneficial improvement of the invention by means of the fact that the treatment apparatus and the fill system are completely sealed against the ambient atmosphere while permitting the liquids to flow directly from the supply tanks through appropriate valves and hose connections into an apparatus completely encased except for discharge opening and additional vent hole. In this case, the liquids can be drained using a pump in a recognized manner from the incubation apparatus into a "sump tank." When refilling, the displaced gas is discharged through a hose connector to the vent hole into the hood or, in another manner, out of the compartment. In a similar manner, this vent hole makes it possible to add skin-toxic media, especially, activated monomer preparations, for polymerization embedding from flexible disposable plastic flasks. These generally viscous liquids are emptied directly into the system of the treatment apparatus by compression of the flask, which is discarded after emptying. For treatments at very low temperatures, below $-20°$ C., as are necessary for dessication of frozen specimens within the framework of cryosubstitution, the entire apparatus can be suspended in the gas compartment of a partially filled Dewar flask in which the gas, which continuously evaporates from the liquid cryogen, causes cooling.

Other advantages and characteristics of the invention are derived from the following description of preferred applications compared to a known device to generate the necessary liquid circulation using attached drawings.

IN THE DRAWINGS

FIG. 2a shows a lateral cross-section along line IIa—IIa in FIG. 2;

FIG. 2b shows a longitudinal cross-section through a specimen holder;

FIG. 3a shows a lateral cross-section along line IIIa—IIIa in FIG. 3;

FIG. 3b shows a lateral cross-section similar to FIG. 3a with a modified insert;

FIG. 4a shows a disposable flask for use in the apparatus as per FIG. 4; and

DESCRIPTION OF THE PREFERRED EMBODIMENTS

Figure 1:
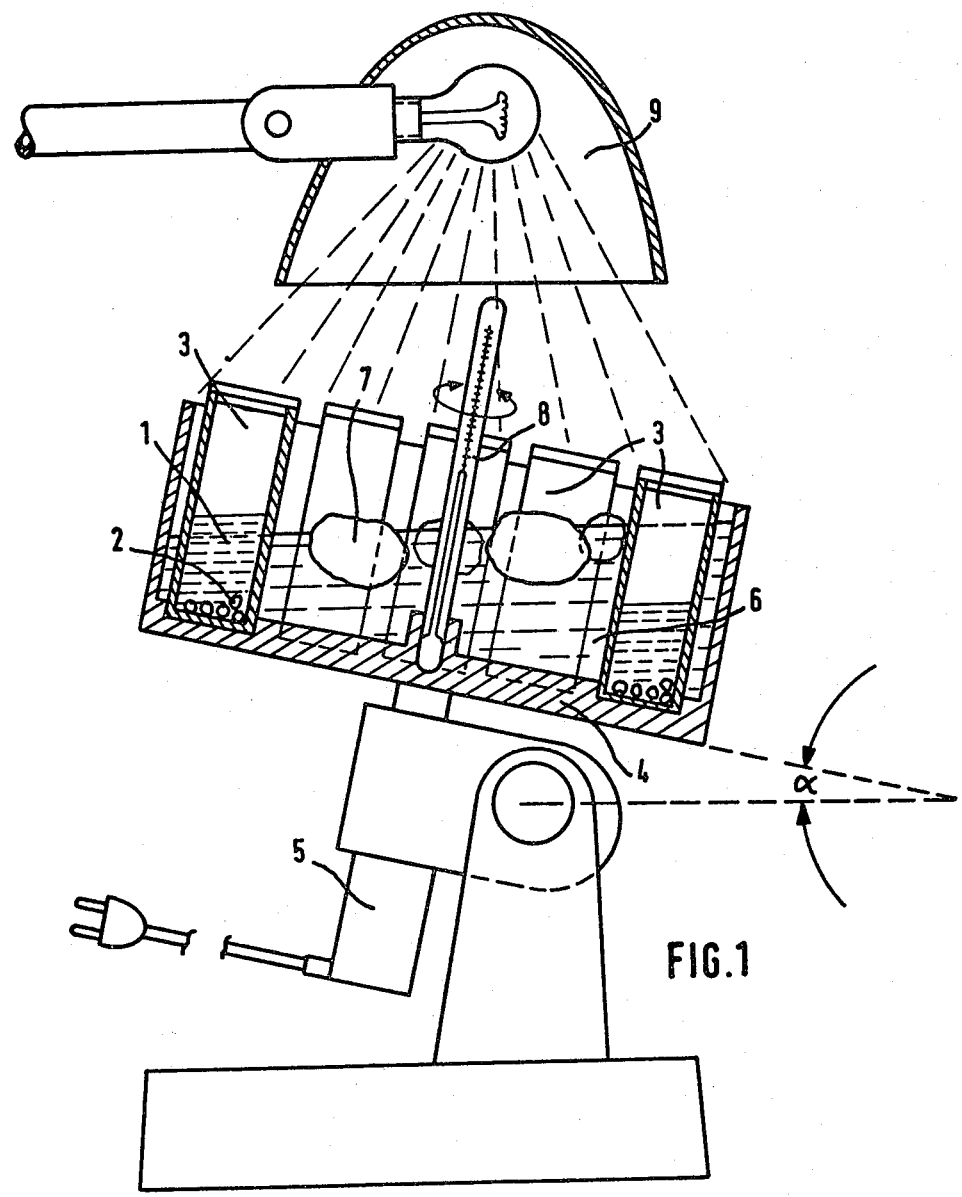
FIG. 1 shows a schematic representation of a rotary disc of a recognized type to generate liquid circulation during treatment with a simple heating and cooling device for treatment at reduced or increased temperature.

FIG. 1 shows a conventional apparatus which generates continuous, gentle, and reproducible circulation of liquids 1 around the likewise slowly moving specimens 2 by means of slow, when necessary reversible, rotation of tank 3 filled successively with liquids 1 for fixation, dessication, and embedding of specimens 2 on rotary disc 4. Rotary disc 4 which is supported on a base, having angle $\alpha$ of tilt which can be varied, is moved in this case by a drive motor 5 with reducing gear. For treatment at reduced temperature, the entire apparatus can be placed in a refrigerator, for treatment at a higher temperature, in an incubator. There exists the capacity shown in FIG. 1 to fill rotary disc 4 in the form of a tank with cold water 6 which can be reduced by ice cube 7 to the desired temperature which can be read on thermometer 8. In a similar manner, this water bath 6 can be heated by a radiator located directly overhead, for example, an office light 9, in which case an extremely uniform temperature distribution is achieved in water bath 6 by continuous rotation of the disc. Overall this simple system allows very gentle and reproducible circulation of liquids and thus optimum penetration of treatment liquids 1 into specimens 2. The remaining operating input for the aforementioned preparation process, however, remains unchanged, as in the conventional techniques, and is even considerably increased in operation in water bath 6. In this case, not only all tanks 3 must be emptied in the stipulated time intervals and refilled, but they must also be carefully drained of water since any remaining water can seriously disrupt the process of dessication and embedding. Therefore, various attempts have been made to adapt known techniques and operating modes of automatic embedding apparatus to the requirements of smaller laboratories, however, especially for the treatment of electron microscopic specimens with extremely small dimensions or pure specimens for light optical research and individual examinations. The success of these efforts has been minimal in the meantime, so that currently hardly any mechanical aids are available for these purposes in which purchase of expensive automatic embedding apparatus does not seem feasible, except for the apparatus shown in FIG. 1.

Figure 2:
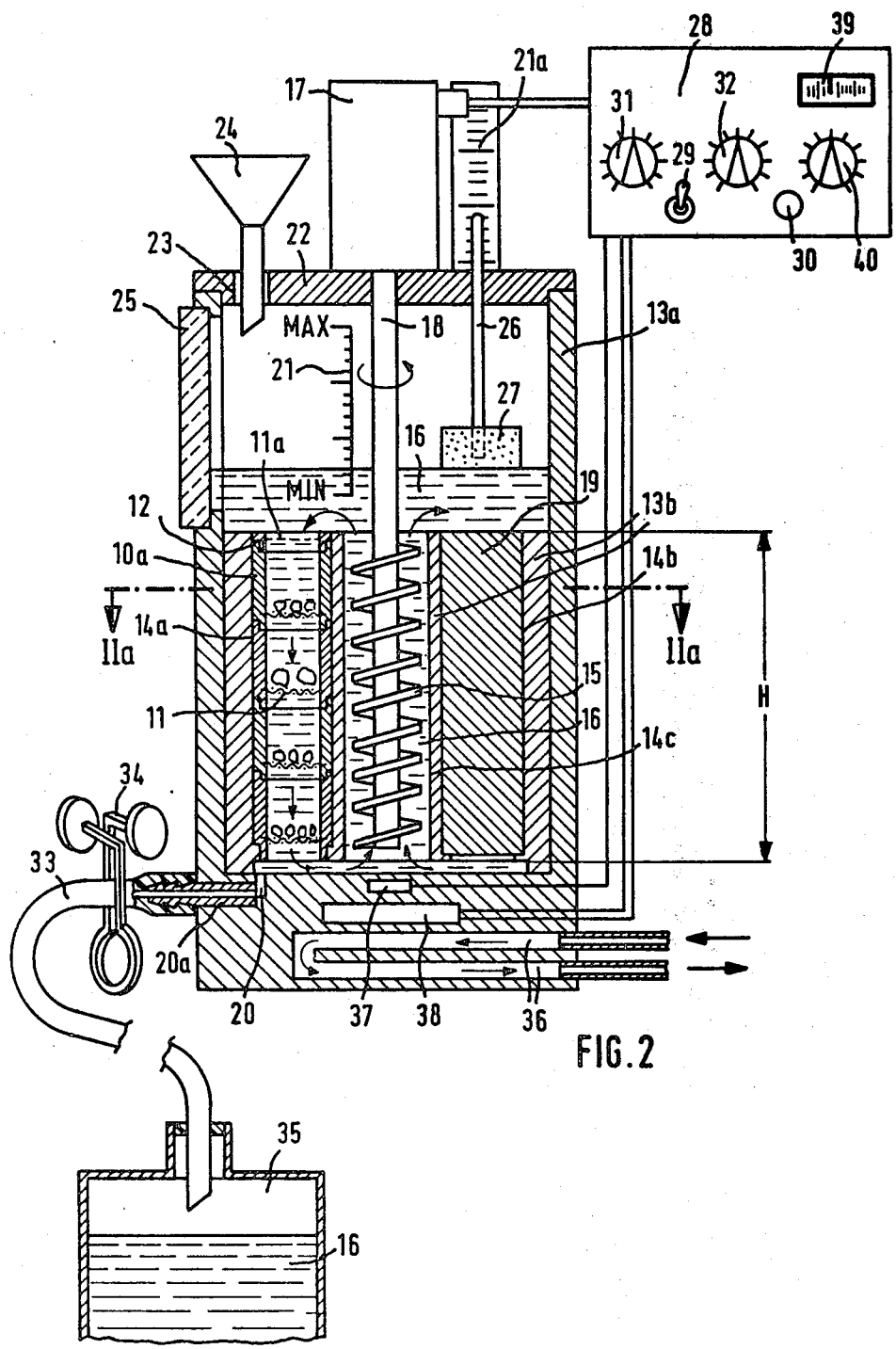
FIG. 2 shows a longitudinal cross-section through a treatment apparatus according to the present invention with auxiliary equipment shown on the same device, which however, can be used as an alternative, in conjunction with cooling or heating by a circulating liquid or circulating gas.

The suggested apparatus which derives from variations and combinations with extent technical equipment schematically shown in FIGS. 2 through 5 conversely simplifies preparations to a considerable degree with a technical input which does not exceed the input of a rotary table as per FIG. 1. A configuration of specimen holders 10 which can be stacked and include at least a partially permeable bottom formed, for example, by mesh 11 is common to the designs shown below, in which case the floor of the holder directly overhead seals the space of the underlying holder and thus prevents loss of specimens 2a. In this case the upper specimen holder 10 fits into the next lower specimen holder with a collar on its bottom end (compare FIG. 2a in this regard). Loss of specimens from the uppermost holder 10a open at the top can be precluded in a varied, technically recognized manner, for example by a partially permeable screw cover 11a (see FIG. 2) or a permeable cover provided with collar 12 (FIG. 2b) or a corresponding component of the treatment apparatus. When specimen holder 10,10a is used, tank 13a with an interchangeable insert 13b as per FIG. 2 is employed in a simple manner. Insert 13b has at least two cylindrical cells or receiver tubes 14a,14b for tank 10 as well as another cell 14c to accomodate a mechanical element 15 to generate a flow of the treatment liquid 16. The lower end of insert 13b contains a rotary rim so that a liquid filled space is formed between it and the base of the tank 13a (see FIG. 2). The cells or tubes 14,14b,14c are open to the space. FIG. 2 shows a screw or a propeller 15 which is turned via a shaft 18 by an electric motor 17. Both the direction of rotation and the rpm can be changed automatically when required in a preselected manner within certain time intervals, for example, by a series connected resistor and commutator. Turning element 15 circulates liquid 16 in the manner shown (arrows) and thus causes uniformly efficient and gentle treatment of specimens 2a. The amount of liquid necessary for this purpose can be reduced almost to the volume of the receiver tube used and that of another tube 14c with the mechanical element 15 by means of the fact that all unused receiver tubes 14a,14b are filled by floats 19 as per the invention. The "empty volume", i.e., the volume of the nonessential liquid, can be reduced to milliliters due to the fact that the gap in the mm order of magnitude is below insert 13, that an outlet pipe 20 to the liquid has a diameter in the mm range and that the liquid is added only up to the "MIN" mark of scale 21 in the tank compartment above insert 13b. If the full height H of a receiver tube 14a with holders 10 is not filled, the remaining compartment can be filled with floats 10b (see FIG. 3) which has a hole of a diameter which still allows sufficient liquid flow.

According to FIG. 2, other suggested characteristics are the aforementioned drain hole 20 and a top hole of tank 13a which is released in the simplest case by the fact that cover 22 is removed upwards with motor 17 mounted thereon, including shaft 18 and element 15. Here scale 21 is visable which allows reproducible filling of the incubation apparatus and can read at the same time the minimum and maximum levels of the liquid ("MIN" . . . "MAX"). Alternatively, liquid can be added through a hole 23 in cover 22 which can be sealed during operation by means of a funnel 24 or other suitable tool (compare FIGS. 3 and 4) without removing cover 22. The liquid level can thus be checked by a viewing glass 25 in the side of tank 13a which may include a scale similar to 21 or by a dip stick 26 with a float 27 by means of scale 21a.

Other modifications of the apparatus as per FIG. 2 may consist in that a special operating mechanism 28 is provided which includes not only an ON-OFF switch 29 and operating indication 30, but also setting wheels to vary the rpm of motor 17 and adjust the time interval by which the motor reverses its direction of rotation and thus changes the direction of liquid flow.

Liquid can be drained in an extremely simple and quite adequate manner by a hose 33 which plugs onto a drain nozzle 20a and which can be opened and closed by a hose clamp 34. Used liquid can thus be discharged without any danger of skin contact directly into a high volume storage tank 35 ("sump") which allows simple disposal of toxic reagents.

The suggested apparatus can be cooled or heated in a circulation process by cooled or heated liquids or gasses by a circulating system 36 in an extremely simple manner in contrast to the rotary disc as per FIG. 1. For example, system 36 can be connected to standard cold and/or heat thermostats with liquid circulation. An alternative modification of the invention, according to FIG. 2, consists in that the treatment apparatus contains a thermometer probe 37 and a heating cartridge 38 which are connected to operating mechanism 28 and thereon allow temperature to be read on indicator 39 and variation of thermal output by means of control button 40. In another modification, an operational link between elements 37,39, and a thermostat for heating and cooling device connected to circulation system 36 can ultimately exercise thermostatic temperature control in a likewise recognized manner.

If we compare the suggested apparatus with the rotary cable as per FIG. 1, the decisive technical advantages of the system become immediately apparent according to FIG. 2: on the proposed system as per FIG. 2, a number of separate holders 10 can be filled and emptied in one procedure, regardless of the number of different specimens 2a, while on the other hand, the apparatus as per FIG. 1 necessitates separate filling and emptying of each of the vessels. In the case of completely equivalent circulation of the liquid, filling and emptying are, moreover, facilitated by corresponding openings and readings. The compact design as well as limitation of motion to components 15,17,18, or equivalent recognized mechanical elements (not shown) also facilitate utilization in unhampered manner with commercial cooling and heating devices, for example, refrigerators and thermostats as well as water baths. Discharge and removal of toxic reagents is possible in a simple manner ultimately by direct drainage of the chemicals used into a disposal tank 35 ("sump") without any other contact of operating personnel with these substances. The same applies to cleaning of the apparatus after use which is largely automatic by adding a suitable solvent and which is completed after draining the rinsing liquid into sump 35.

Figure 3:
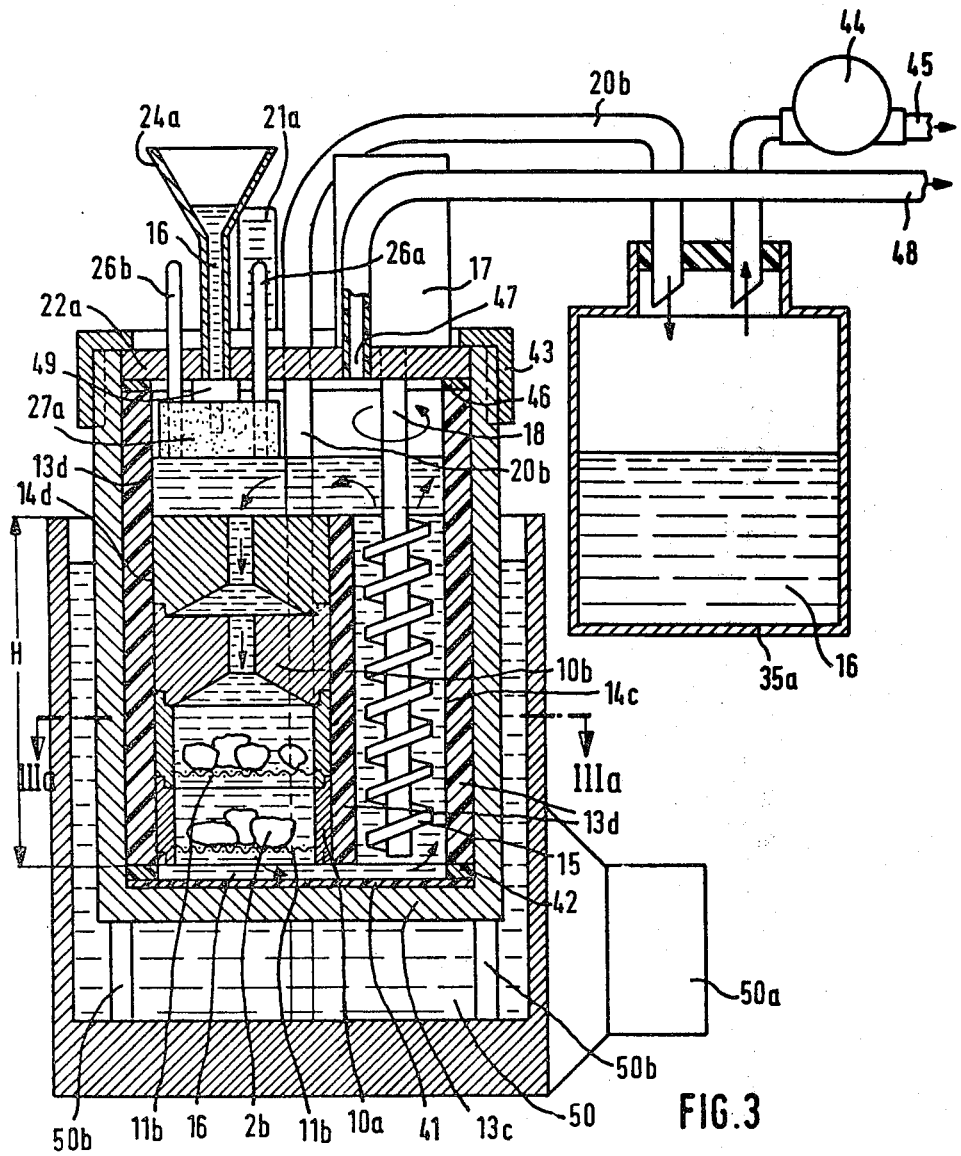
FIG. 3 shows a schematic representation of a modified design of the incubation apparatus with cooling and heating of a different type.

FIG. 3 shows alternative designs and improvements of the invention. In this form, tank 13c is of a metal with good thermal conductivity, insert 13d however, of an inert plastic which neither reacts with the liquids 16 used, or is corroded by them, and can be easily cleaned due to its surface composition. Good heat exchange between the treatment liquid 16 and metal jacket is achieved by means of a thin sheet 41 as the base of the compartment which is closed against the metal jacket of tank 13c by seal 42 between components 13d and 41 and which consists primarily of plastic insert 13d. Insert 13d shown in FIG. 3 allows a combination of narrower holders 10 as well as wider holders 10a for larger specimens 2b by means of receiver tubes 14d and 14e with varied diameters A and B.

When necessary, insert 13d can be replaced by insert 13e which is shown in cross section in FIG. 3b which includes, exclusively, receiver tube 14e with the smaller diameter B at an identical configuration of tube 14c for element 15. Thus, the apparatus can be used with insert 13d to treat large and/or small blocks and, alternatively with insert 13e to treat a considerably larger number of small blocks. The number of possible modifications can be varied arbitrarily at appropriately selected dimensions of inserts 13c,13d, and thus adapted to any specific need. In addition to the aforementioned floats 9, unused places for specimen holders 10 or 10a can be occupied by blanks 10b.

In another configuration of the invention, the liquid can be changed as per FIG. 3 by the fact that a discharge tube 20b runs upward through cover 22a secured, for example, by a screw collar ring, and that the liquid is drained off into a large volume storage tank 35a by means of the pump, in which case possible toxic vapors are discharged by the pump through hose 45 from the work space.

Treatment compartment can be completely sealed against the ambient atmosphere by a second sealing ring 46 between insert 13d and cover 22a. In this case, vent hole 47 with hose connection 48 makes it possible that the sealed incubation compartment is always in a pressure balance with the atmosphere without toxic vapors escaping into the ambient atmosphere when adding new liquids.

Finally, in an improvement of the design as per FIG. 3, overfilling of the apparatus is prevented by an operational link between fill level indicator 26a,27a and fill device 24a due to the fact that an interchangeable stopper 49 seals the fill hole just as the desire standard level of maximum level of liquid is reached. A minor excess possibly already added can, in this case, be admitted by light pressure on bolt 26 still in the incubation compartment in which case the fill hole automatically recloses afterwards by the buoyant force of float 27a.

The configuration shown in FIG. 3 allows the simple possibility of temperature control by means of a commercial laboratory water bath 50 with water temperature regulation 50a by a thermostat. Tank 13 is placed on supports in the water bath.

Figure 4:
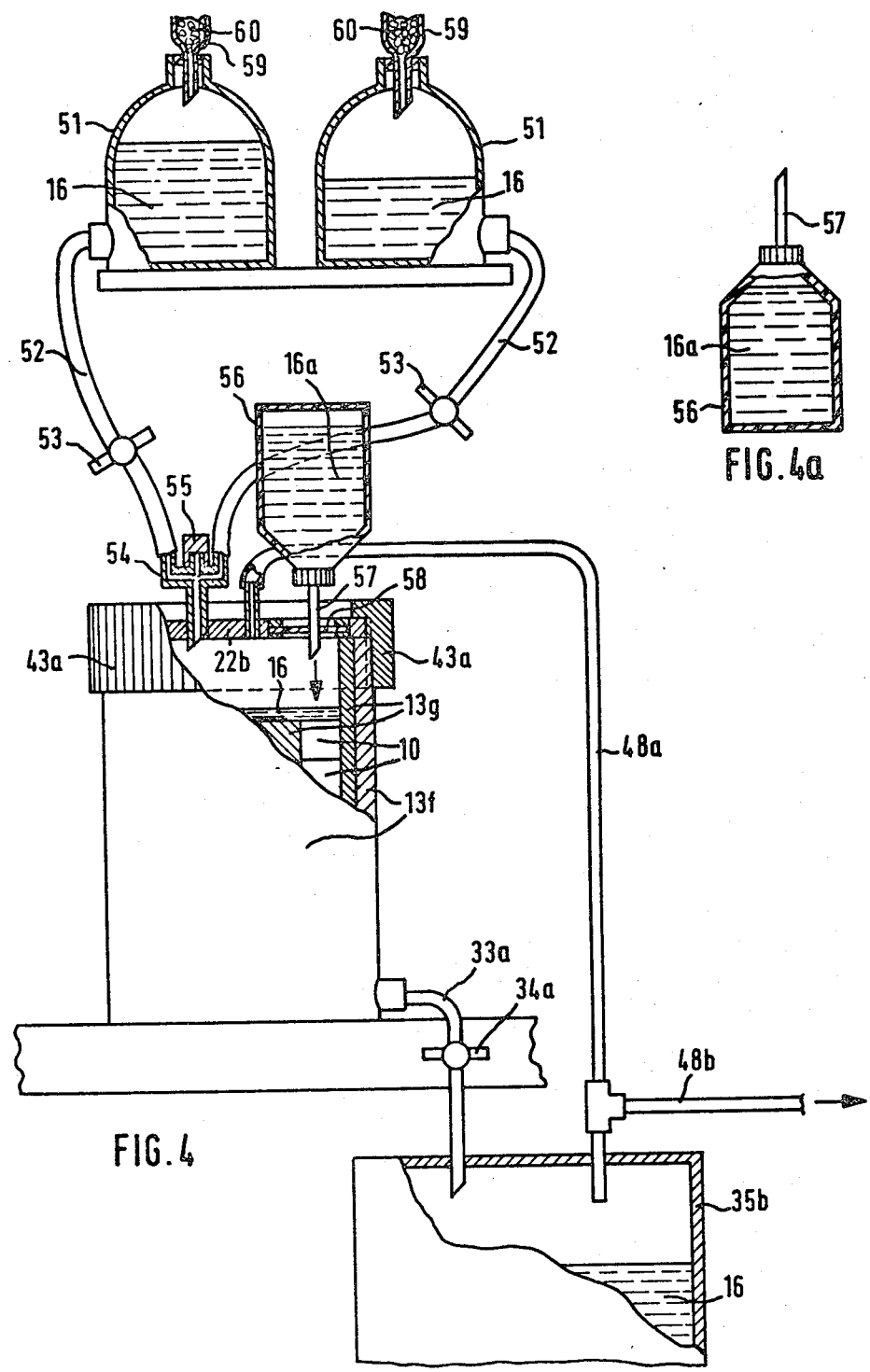
FIG. 4 shows a schematic representation of an improvement of the apparatus of FIGS. 2 and 3 with ventilation and fill devices which avoid skin contact and inhalation of toxic vapors.

FIG. 4 shows an improvement of the apparatus as per FIGS. 2 and 3 for routine operations with liquids 16 and with viscous liquids 16a, for example, activated monomer preparations with which any skin contact or inspiration of toxic vapors must be avoided. The completely sealed apparatus 13f, for example as per FIG. 3, the details of which are not fully represented in FIG. 4 for the sake of simplicity (compare FIGS. 2 and 3) is tightly sealed with cover 22b by tightening screw cap 43a after specimen holders 10 are filled. From this moment on any contact with the media 16,16a hazardous to operating personnel is prevented. Low viscosity liquids 16 are decanted into the treatment compartment from storage tank 51 via hoses 52 and hose spring clip 53 and a collector piece 54 with multiple connections or a comparable element. In this case unused connections to collector piece 54 are sealed by caps 55. Mixing of liquids from the different storage tanks 51 can easily be minimized in a recognized manner by the very small inside diameter of the lines in the collector piece as well as by purging a prior run. Viscous liquids 16a can be decanted after application into flexible plastic disposable flasks 56 with hollow connector needles, stored at low temperature and then reheated to room temperature before use.

Liquid 16a is decanted in a recognized manner (for example penetration of an elastic membrane) by squeezing out plastic container 56 which is removed and discarded after emptying. As we know from clinical practice (storage bottles with injection solution) this kind of membrane 58 can be punctured several times before replacement is necessary. After opening hose clamp 34a, liquids used are drained through hose 33a into the storage tank which is ventilated jointly with the incubator via hoses 48a,48b. Storage bottles 51 are ventilated, if necessary, in a recognized manner through tubes 59 which are filled with a suitable absorbent.

Figure 5:
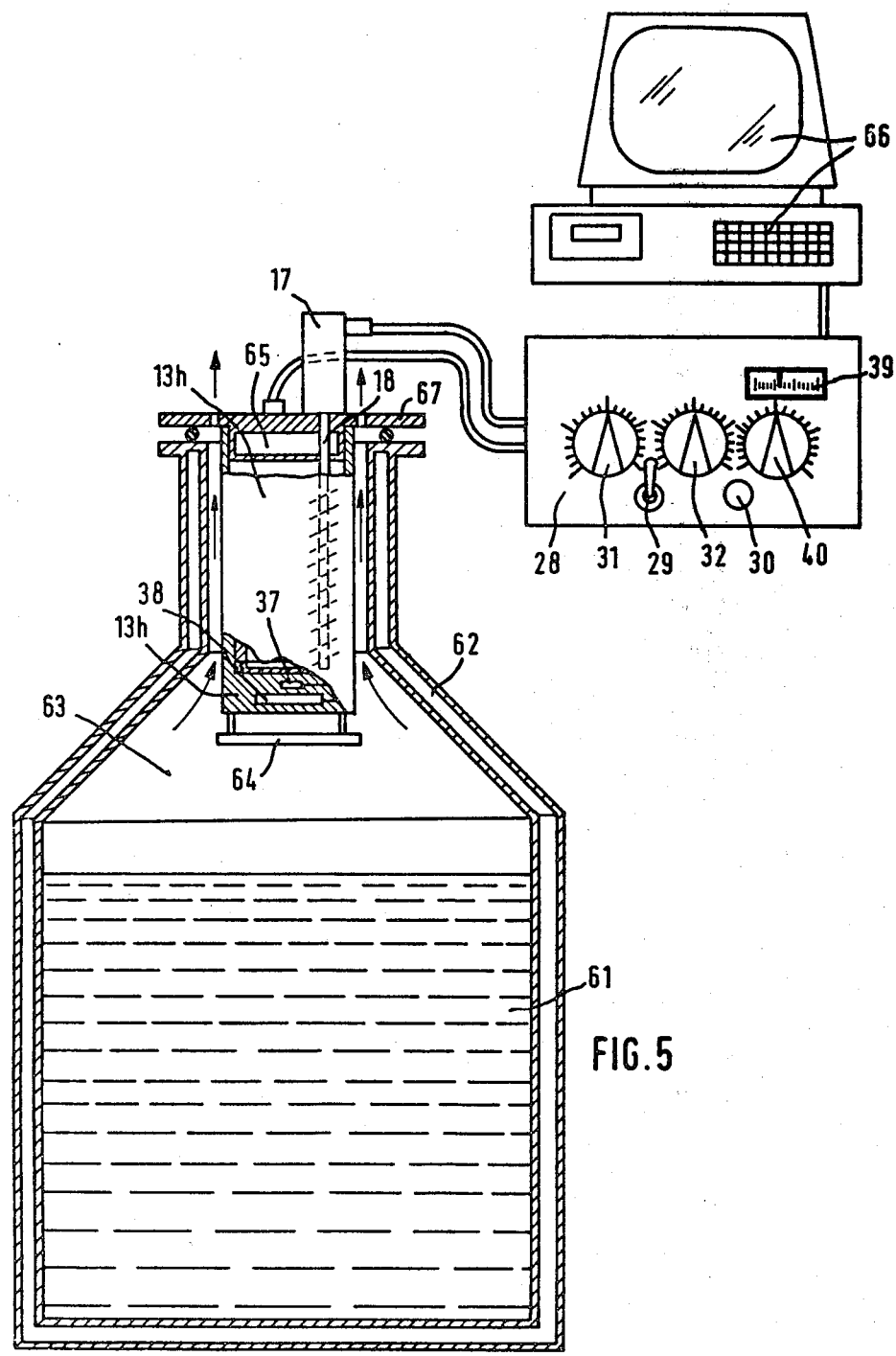
FIG. 5 shows a schematic representation of a configuration of the apparatus in conjunction with a Dewar flask partially filled with a liquid cryogen for dessication of frozen biologic specimens temperatures below $-20°$ C.

An example of the possible use of the proposed apparatus at low temperatures in combination with an already existing cooling configuration is shown in FIG. 5.

Because of small size, the proposed apparatus can be used, in this case, to dessicate cryofixed, frozen, biologic specimens at temperatures in the range between −80° and 10° C. in exact analogy to dessication of chemically fixed biologic specimens in a beneficial manner in combination with a cooling system by placing tank 13h in the neck of a Dewar flask 62 partially filled with liquid cryogen 61. In this case, the gas 63 which continuously evaporates from cryogen 61 and escapes through the narrow gap between tank 13h and the neck of the Dewar flask 62 (arrows) cools the tank when an insulated filler 64 is used low enough without perceptibly increasing the vaporization rate of the cryogen thereby. After completion of dessication the temperature of the tank 13h measured in the aforementioned manner by components 37,39, can be raised by heating element 38. Without changing the position of tank 13n the embedding medium can be transferred to the specimens after the dessication medium is drained. A disruptive rise of vaporization rate of cryogen 61 is prevented in this case by a thermal insulation shield 64 with reflective coating which is connected to the bottom of tank 13h. The process which continues over several days or weeks can be controlled by means of tape in a recognized manner by a computer 66 directly connected to operating mechanism 28. Even the apparatus incompletely shown in FIG. 5 with tank 13h fastened to the Dewar cover 67 by installation 65 is identical to one of the designs as per FIGS. 2 through 4 in terms of internal structure and function.

The design variations and application described using FIGS. 2 through 5 show the range of application and adaptability of the proposed system to the varied demands of research and routine. Moreover, the invention can be built in numerous combinations and variations not shown and/or described. For example, it is possible to achieve the same effect of liquid flow both reversible and variable in strength using mechanical elements other than those shown. It is unimportant in what manner and of what parts the apparatus is composed and whether, for example, the base of the housing is constituted separately or in the manner described a single piece 13a or 13c,13f or 13h. Shape, diameter, and configuration of the tube system can be adapted to the individual purpose in one with the receiver holders and thus can be constituted in the most varied manner without loss of the characteristic features of the proposed apparatus. Nor is it important for the invention which materials are used in an appropriate adaptation to the specimens and media employed. Heating, cooling, and exhaust devices, as well as valves, fill devices, and readings represent integrating elements of the invention, however, they can be implemented in a varied manner. The same applies to the entire electrical system.

The receiver cylinders or cells for the specimen holder in the application examples are shown as mutually parallel recesses of the insert. This parallelism is, however, in no way obligatory; nor is the vertical orientation of the receiver cylinder important. Rather, a configuration slanted against the vertical is possible.

In addition, the insert in which the receiver cylinders are constituted in the form of cells can also be designed differently, for example in the form in which the receiver cylinders in the form of separate tubes are arranged in a rack, the top and bottom ends of which discharge into an overflow compartment separately for each.

I claim:

1. In apparatus for fixation, dessication, and embedding of biologic specimens for microscopic, especially electron microscopic studies, having a compartment for treating specimens held in liquid permeable specimen holders, a supply of treatment liquid, means connecting the supply to said compartment, and means to introduce liquid from the supply, and remove liquid from the compartment, the improvement comprising a chamber (14c) in said compartment for holding a quantity of fluid, a passage connected to said chamber, pump means (15) located in said chamber for moving fluid through said passage, at least one tubular cell (14a) for supporting a plurality of specimen holders (10, 10a) in an end to end relationship, one end of said cell being connected to said passage, the other end of each of said chamber and said cell being connected to a common portion of said tank to permit liquid to be circulated by said pump means.

2. The improvement of claim 1 having a plurality of cells (14a, 14b).

3. The improvement of claim 2 wherein said tubular cells and said chamber constitute an integral unit removable from said compartment.

4. The improvement of claim 1 wherein a cylindrical body (13b, 13d, 13e, 13g) has a plurality of cells (14a, 14b, 14d, 14e) forming parallel cylindrical passages through said cylindrical body and said chamber is a cylindrical passage parallel to said cells in said cylindrical body.

5. The improvement of claim 4 wherein said passage is formed between one end of said cylindrical body and one end of said compartment.

6. The improvement of claim 3 further including means (10b) for displacing liquid from all but a small passage of a portion of at least one cell.

7. The improvement of claim 1 further including means to control the temperature of said compartment.

8. The improvement of claim 1 wherein said pump means includes an impeller located in said chamber and motor means external to said tank connected to said impeller.

9. The improvement of claim 8 further including means for varying the speed of said motor whereby the circulation rate of the liquid is variable.

10. The improvement of claim 9 wherein said motor is reversible.

* * * * *